United States Patent [19]

Alexander et al.

[11] 4,080,837

[45] Mar. 28, 1978

[54] SONIC MEASUREMENT OF FLOW RATE AND WATER CONTENT OF OIL-WATER STREAMS

[75] Inventors: John D. Alexander; Philip W. Reed, both of Ponca City, Okla.

[73] Assignee: Continental Oil Company, Ponca City, Okla.

[21] Appl. No.: 747,170

[22] Filed: Dec. 3, 1976

[51] Int. Cl.² .......................................... G01N 29/02
[52] U.S. Cl. .................................. 73/61.1 R; 73/597; 73/645
[58] Field of Search .................... 73/53, 61 R, 61.1 R, 73/194 A, 560

[56] References Cited

U.S. PATENT DOCUMENTS

| | | | |
|---|---|---|---|
| 3,171,095 | 2/1965 | Gennari | 73/560 X |
| 3,290,934 | 12/1966 | Brown et al. | 73/53 X |
| 3,973,430 | 8/1976 | Cirulis et al. | 73/61.1 R |

OTHER PUBLICATIONS

W. R. Loosemore et al., "A New Ultrasonic Flowmeter" Ultrasonics, Jan. 1969. pp. 43-46.
E. M. Zacharias, Jr., "Process Measurements by Sound Velocimetry" — Instruments and Control Systems — Sept. 1970, pp. 112-113.

Primary Examiner—Charles A. Ruehl
Attorney, Agent, or Firm—A. Joe Reinert

[57] ABSTRACT

A method and apparatus for metering water content in an oil-water system by measuring sonic velocity in a flowing oil-water mixture, thereafter to determine flow rate to provide individual oil and water rates which may then be integrated to provide oil and water volume of flow. The apparatus functions to provide continual readout of oil and water data by deriving bi-directional speed of sound through the moving medium with subsequent frequency difference processing to derive sonic velocity, flow rate measurement and subsequent integral data output.

9 Claims, 5 Drawing Figures

SONIC MEASUREMENT OF FLOW RATE AND WATER CONTENT OF OIL-WATER STREAMS

BACKGROUND OF THE INVENTION

1. Field of the Invention

The invention relates generally to flow monitoring of oilwater systems and, more particularly, but not by way of limitation, it relates to improved apparatus for maintaining continual readout of flowing oil-water systems to maintain precise content.

2. Description of the Prior Art

The prior art includes several types of flow monitoring apparatus which have been utilized in the past for determining the content of oil and water in production oil well testing procedures and related pipeline conduction wherein oil-water systems may be flowing. Prior methods utilize net oil computers or a related type of net oil analyzer which determine oil and water rates during well testing by utilizing two or three phase separators for subsequent analysis with a capacitance cell. Normally, the capacitance cell is only capable of measuring water content up to about thirty percent, and still further limitations of use are imposed by the degree of continuity of oil present in the system. Capacitance cell output is inherently non-linear and, when other factors contribute, high water contents of fifty percent and over are difficult to measure with any accuracy. U.S. Pat. Nos. 3,780,577 and 3,697,936 illustrate prior art as it relates to particular forms of apparatus for utilizing ultra-sonic energy in flowing fluid systems for determining sonic velocity and related data. Also of interest as a basic, related teaching is a technical article from *Instrumentation Technology*, September 1970, by E. M. Zacharias and entitled "Sonic Monitor for Solution Analysis".

SUMMARY OF THE INVENTION

The present invention contemplates a method and apparatus for determining content data relative to a flowing oil-water system, for example, as may be present at a production well site. The invention utilizes a special pipe section which utilizes a mixer and straightening vane in series for providing fluid to a sonic flowmeter pipe section wherein flowmeter data, as regards sonic velocity and ultrasonic frequency differentials, is utilized to determine not only flow rate and volume but the particular percentage cut of each of oil and water within the flowing system. Thus, output data is continually provided which indicates the percentage cut of oil and water in the conduit, as well as the time integrated rates which provide direct oil and water volume information.

Therefore, it is an object of the present invention to utilize the sonic flowmeter in conjunction with a flowing oil-water system to determine percentage content, flow rate and volume of each of the oil and water components.

It is also an object of the present invention to provide apparatus wherein an all liquid stream can be tested to determine the individual oil and water rates without making a physical phase separation, such testing being accurate over the total zero to one hundred percent water content range.

It is yet another object of the present invention to provide improved apparatus for production well testing which has greater accuracy, greater rangeability, and is more reliable.

Finally, it is an object of the present invention to provide a wide-range, net oil analyzer of the type which may be self-contained on the site to function in conjunction with related computer hardware to provide continual and complete production data having minimal average error.

Other objects and advantages of the invention will be evident from the following detailed description of when read in conjunction with the accompanying drawings which illustrate the invention.

DETAILED DESCRIPTION OF THE INVENTION

Figure 1:
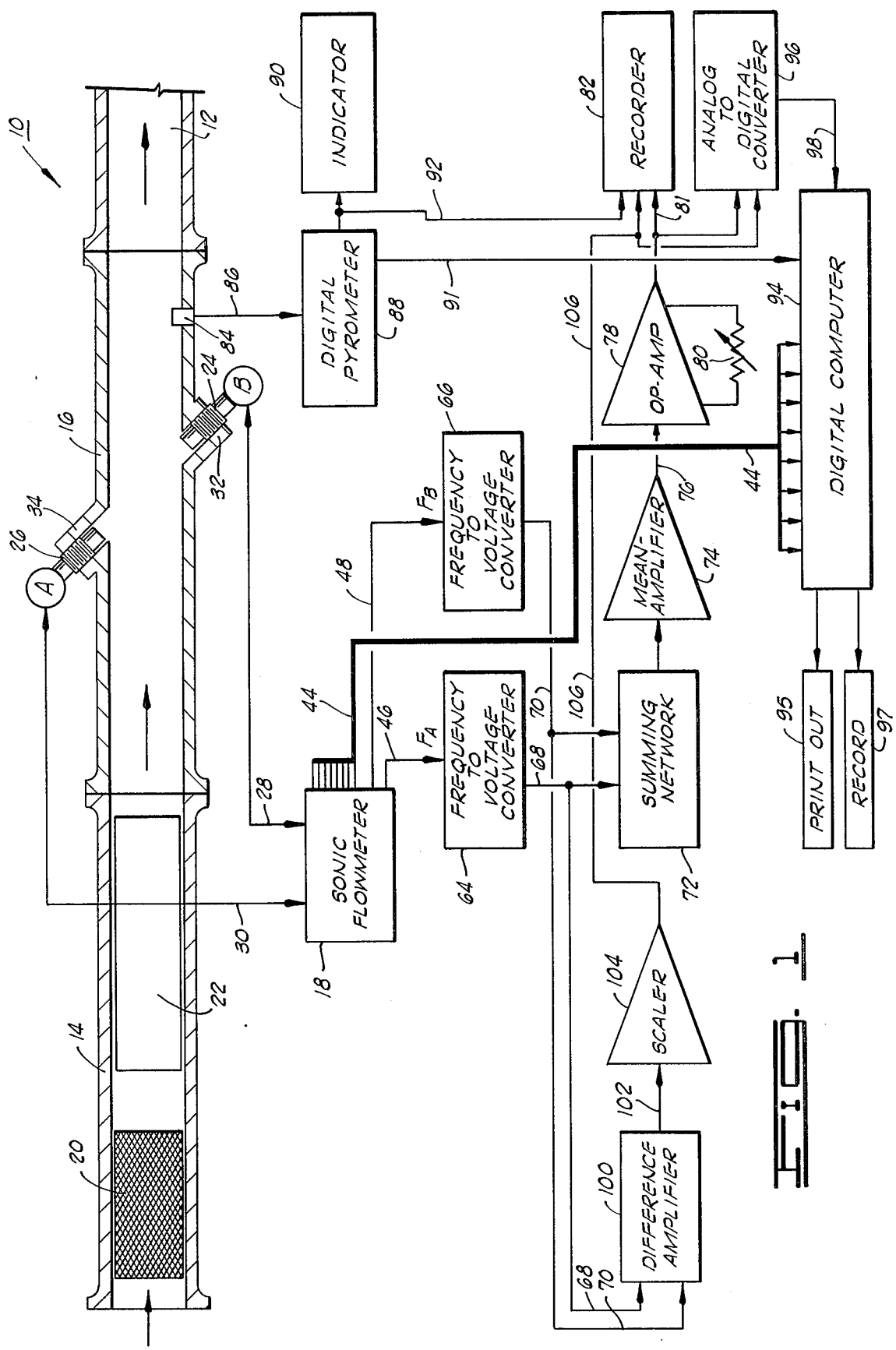
FIG. 1 is a schematic representation in partial block form which illustrates the present invention.

FIG. 1 illustrates a conduit or pipe 10 which is carrying a mixture of crude oil and water 12 as may be found at an oil well production site. In such cases, the proportion of oil versus water is known with but little accuracy, yet it is important to verify due to various exigencies of production testing, operator accounting information, equipment maintenance and general information required of such installations. A pipe section 14, which includes mixing structure, is placed in the flow system just prior to the metering pipe section 16 which includes sensing and transducer devices for a sonic flowmeter 18.

The mixing pipe section 14 includes a Koch mixer 20 followed by an assembly of straightening vanes 22, which are suitably secured sufficiently, to resist the force of fluid flow, by conventional fasteners or by special adaptors such as set screws inserted through the pipe wall and sealed with plugged THREDOLETS. The Koch mixer is a commercially available device which is manufactured by Koch Engineering Company, Inc. and is known and described technically as "Koch static mixing element". The mixing element 20 merely consists of a metallic filter adapted to specific pipe size which consists of a plurality of tortuous flow routes therethrough. The tortuous route or cell sizing is related to the number of cells per cubic foot and determines, along with relative flow velocity, the droplet size in the output oil-water mixture. The mixed and turbulent flow exiting from mixer 20 is then aided by an assembly of straightening vanes 22 which merely function to reduce flow disturbances for entry to the metering pipe section 16. Straightening vanes 22 may consist of an assembly of plural, parallel flow tubes of proper diametric size as suitably secured in the pipe section 14 by conventional fasteners. Such straightening vane assemblies are available from Daniel Industries, Inc. of Houston, Texas. Alternatively, a formation of parallel plates may be utilized.

The metering pipe section 16 includes a frequency sensing and transmitting) as located downstream and directed toward a counterpart frequency sensing and transmitting transducer A(26), each of which provide electrical connection by respective leads 28 and 30 to a sonic flowmeter 18. Threaded feed-through fixtures 32 and 34 may be secured, as by welding, diagonally and in-line across pipe metering section 16 to provide the requisite ultrasonic energy interaction, as will be further described. The sonic flowmeter 18, including the requisite frequency sensing and transmitting transducers, is a commercially available equipment which is obtainable from MAPCO, INC. of Tulsa, Okla., and such commercial device is shown in general block form in FIG. 2.

Figure 2:
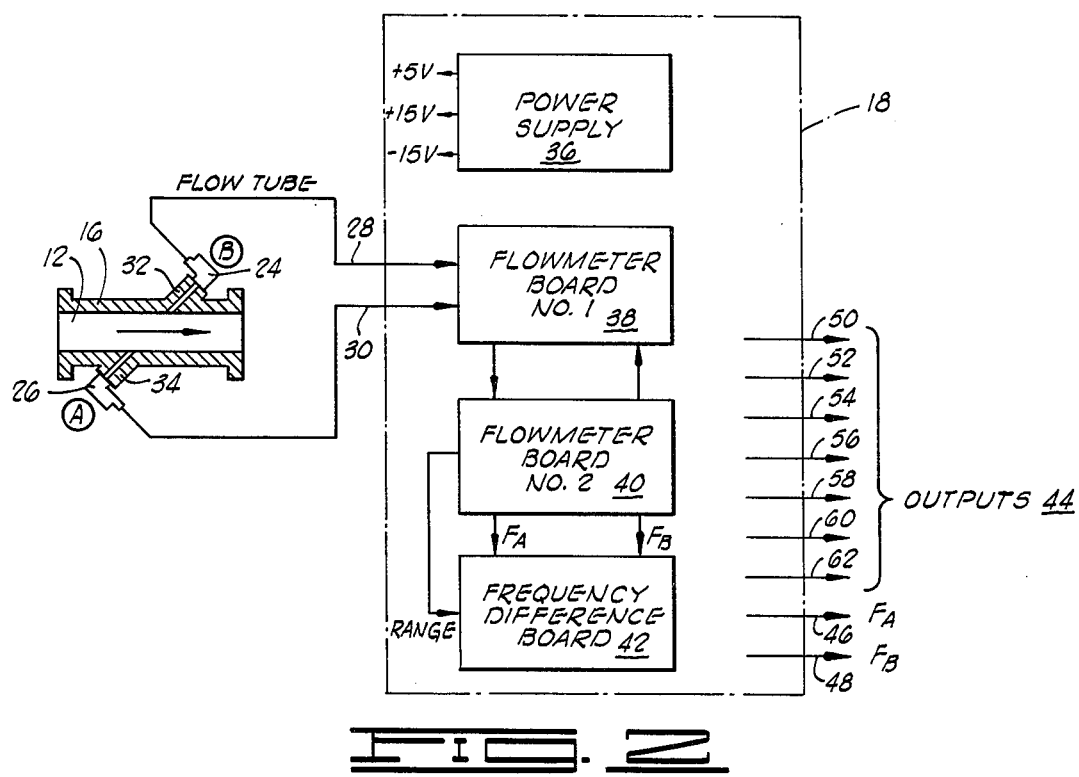
FIG. 2 is a block diagram of flow analysis apparatus as utilized in the present invention.

Referring now to FIG. 2, the basic structure of sonic flowmeter 18 consists of a standard form of power supply 36, and an input circuit board or flowmeter board number 1, designated 38, which conducts the frequency information via connectors 28 and 30. A flowmeter board number 2, designated 40, is connected interactively with flowmeter board 38 while providing range, Fhd A and $F_B$ output data to a frequency difference board 42. Effectively, flowmeter 18 operates by determining the speed of sound in the upstream direction and the speed of sound in the downstream direction. In one case, the flow velocity of the liquid to be metered is substracted from the liquid's inherent speed of sound and in the other case the flow velocity is additive. When the two sonic velocities determined by the instrument are electronically subtracted one from the other, the inherent speed of sound of the liquid medium cancels itself out and the difference is relatable to the average liquid velocity.

An electrical initiation pulse conducted from flowmeter board 38 via connector 28 to transducer B triggers transmission of a sonic pulse which travels through the liquid in the pipe section 16 to transducer A(26). Transducer A(26) receives the sonic pulse and converts it back into electrical energy for conduction via connector 30 for input to flow board 38 and subsequent electronic detection which generates yet another pulse to trigger transducer B(24). The result is a continuous series of pulses traveling from transducer B to transducer A, and the frequency of these pulses is essentially proportional to the velocity of sound between transducer B and transducer A traveling in the direction of transducer A. This constitutes the frequency designated as $F_B$.

On a shared time basis, a similar train of pulses is generated in the opposite direction with transducer A transmitting and transducer B receiving. This frequency, when detected and processed, is designated $F_A$ as derived for ultrasonic energy traveling downstream in the direction of transducer B. It can be shown that when these upstream and downstream frequencies are subtracted one from the other, the following expression results:

$$v = f/K$$

Where:

$V$ is equal to the flow velocity in the pipeline in distance per unit time (e.g. feet per second);

$f$ is equal to frequency difference in pulses per second which is equal to $F_B - F_A$; and $K$ is equal to a constant, which is directly proportional to pipe diameter and also a function of the specific electronic design and flow pipe section geometry.

The sonic flowmeter 18 provides a plurality of outputs 44 as well as raw frequency $F_A$ and $F_B$ outputs via connections 46 and 48. Outputs 44 include individual output connections 50, 52, 54, 56, 58, 60 and 62 which provide the following data. Output 50 provides instantaneous flow rate in terms of frequency; output connection 52 presents an output flow rate in terms of average frequency $a$ as averaged over a preselected time period which is adjustable; output 54 provides an analog voltage output which varies proportionally to frequency $f$ from zero volts to +10 volts DC and is indicative of flow rate; output 56 provides flow rate in the form of a calibrated analog current; output 58 provides an indication of flow direction as between the transducer B upstream and transducer A downstream sources; output 60 controls a self-test light emitting diode which is normally extinguished, but is illuminated to indicate malfunction; and, output 62 indicates transmitted ultrasonic energy attenuation for further malfunction protection.

Referring again to FIG. 1, outputs in sonic flowmeter 18 are used variously to determine output data and other system characteristics for analysis of the oil-water system. The frequency $F_A$ and $F_B$ as output on connectors 46 and 48 are applied to frequency to voltage converts 64 and 66, respectively. The frequency to voltage converters 64 and 66 may be conventional forms of circuitry which serve to signal at designated input frequency to provide output of an equivalent or proportional analog voltage via respective leads 68 and 70. In simplest form, the frequency to voltage converter may be an integrator circuit operating into a sample and hold amplifier with clocked output, but many other forms of highly reliable frequency to voltage conversion circuit are available in the integrated circuit forms. The analog voltage output on leads 68 and 70 are applied to a summing network 72 at the input to a mean amplifier 74 which provides analog output on lead 76 which is the mean or average analog value as between the $F_A$ and $F_B$ analog signals. The average analog voltage on lead 76 amounts to the average frequency as between $F_A$ and $F_B$ which is a signal proportional to the speed of sound in the oil-water medium.

The proportionate speed of sound voltage on lead 76 is then applied to an op-amp 78 functioning on a scaling circuit and including a zero or base calibrator feedback potentiometer 80. The scaled proportional output signal from op-amp 78 is then applied to a suitable form of recorder 82 of the type which is well-known in the oil field, geophysical and related arts. Recorder 82 may constitute any direct readout recorder such as ink pen, camera or the like, and such output may be further recorded on magnetic tape for storage or transmittal to a central laboratory for further processing. Additionally, meter readout may be provided on site for instantaneous monitoring.

Simultaneous with derivation of the speed of sound data is sensing and recording of the temperature of the flowing oil-water medium since, as will be further discussed below, the flowing medium temperature exhibits great effect on output data. Temperature may be sensed by a suitable sensor attachment 84, e.g. a platinum resistance temperature detector, or the like which is sealably inserted into the wall of meter pipe section 16 in contact with the flowing medium to provide output by a connector 86 to such as a digital pyrometer 88. An analog output from digital pyrometer 88 may be directly applied to a suitable meter or other indicator 90 as well as in parallel via lead 92 for input to the recorder 82 in synchronism with the simultaneously derived average frequency or sound velocity data.

A suitable digital pyrometer is commercially available from Newport Laboratories of Santa Ana, Calif. and is identified as a Model 267. This unit functions with sensor input from either a thermocouple or a platinum resistance detector and provides direct indicator output and analog voltage output, as well as computer compatible binary coded decimal output as may be directly applied by a lead 91 to a digital computer 94.

Still other and more refined data output can be derived utilizing the digital computer 94 in conjunction with the sonic flowmeter 18 and temperature sensing structure. The digital computer 94 may be a well-known and commercially available type of mini-computer such as the Texas Instruments Model AES 8000, to name but one. Temperature output from lead 91 is applied to digital computer 94 as is the output from op-amp 78 which may be passed through an analog to digital converter 96 of conventional type to provide output on lead 98 in designated format for entry to computer 94. In like manner, and/or alternatively, the plurality of outputs 44 constituting all necessary data outputs (See FIG. 2) may be applied in like manner for input to computer 94 with permanent output provided on peripheral equipment, e.g. print-out 95 and/or Recorder 97. It should also be understood that data processing and output of the desired oil cut information is particularly adaptable to the more recently developed integrated circuit microprocessor circuitry, all integrated process functions being readily programmable into the microcircuit components.

Further analog flow rate information may be derived by taking the analog voltage outputs on leads 68 and 70 for input to a difference amplifier 100. Thus, difference amplifier 100 derives an analog voltage output on lead 102 which is a proportional indication of flow rate V which is then input to a scaler circuit 104 to provide proper calibration in relative bounds for input via lead 106 to a remaining channel of recorder 82. Scaler 104 is adjusted to provide the requisite range and calibration adjustment over the scale of actual flow rates so that the proportionate output on lead 106 will provide direct reading indication as recorded, and be applied to digital converter 96.

Initial calibration of the system of FIG. 1 depends upon the compilation and/or digital storage of empirical data whereupon the system is then capable of electronic calibration for each form of water, i.e., degree of salinity and the like, or of oil product in the mixture. Thus, FIG. 3 indicates a compilation of data which relates to pure water and kerosene of 42° API or relative specific gravity. The graph proceeds in terms of average frequency in KHz, on ordinate Y, versus temperature (F°) along abscissa $x$, and ranging from the pure water indicator line 110 to the 100 percent kerosene indicator line 112. Thus, the dash line 114 would indicate a transgression in terms of average frequency Y for a constant temperature X of 75° for an oil-water mixture ranging from 100 percent water to 100 percent kerosene. It has also been found that the average frequency variation across the range of an oil-water mixture exhibits slight, predictable non-linearity for the water component and linearity for the oil component.

Figure 3:
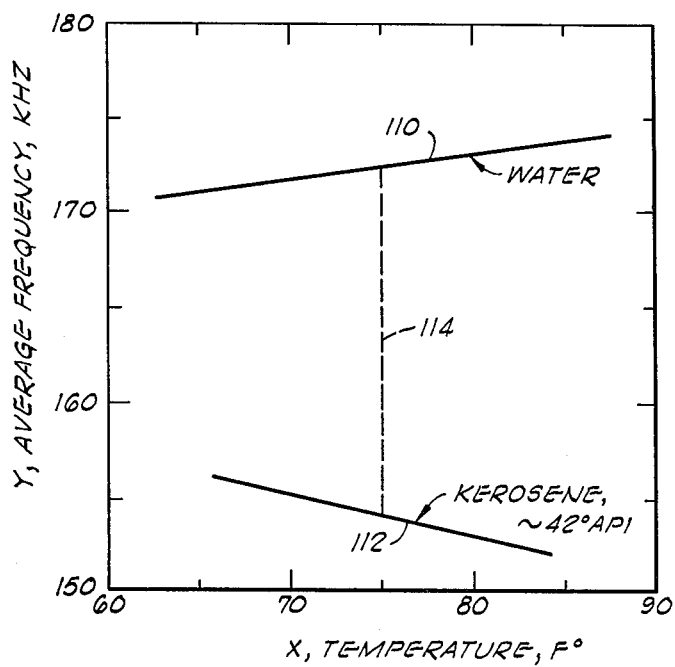
FIG. 3 is a graph depicting frequency variation versus temperature for separate phases of water and kerosene.
Figure 4:
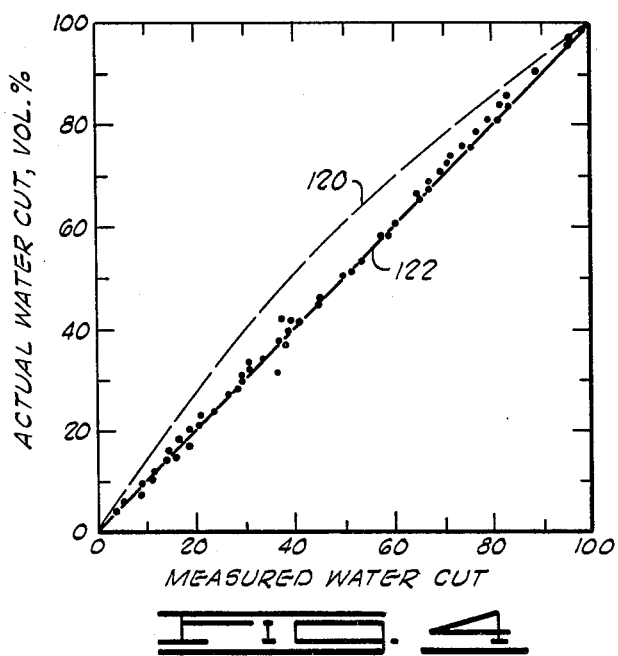
FIG. 4 is a graph depicting the accuracy analysis of actual water content versus measured water cut from zero to one hundred percent.

As regards linearity of data and calibration efficiency of the present method, FIG. 4 illustrates a graph of an oil water mixture wherein the actual measured water cut in volume percent was plotted versus the water cut derived from the present process utilizing sonic flowmeter 18. This initial data as distributed along dash line 120 is linearized by well-known processing to develop the numerous data points which are closely grouped along diagonal line 122. The nature of the water-induced non-linearity for each oil-water system is readily corrected by application of a common and well-known computer routine known as regression analysis wherein a relationship is developed which serves to linearize the results as obtained with the present system. The regression analysis equation used for the oil-water system of FIG. 3 is $$Y = X + A_1 X(X-100) + A_2 X(X-100)^2$$

Where
$X$ is equal to an uncorrected water cut in volume percent; and
$Y$ is equal to corrected or linearized water cut in volume percent. For the particular fluids of the experimental data reported:
$A_1$ is equal to $-0.000380645$; and
$A_2$ is equal to $0.0000239721$.

Figure 5:
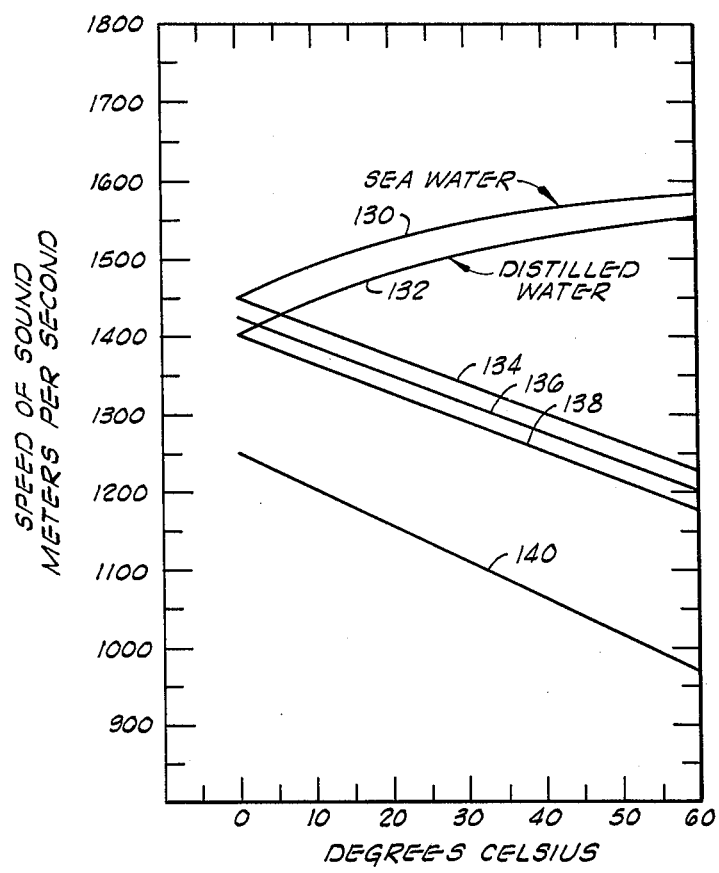
FIG. 5 is a graph of speed of sound versus temperature illustrating the various values of particular oil and water substances.

FIG. 5 illustrates response characteristics for numerous oil and water substances in terms of speed of ultrasonic energy or meters per second versus degrees Celsius. The data is compiled in this illustration from 0° Celsius through 60° Celsius and indicates particularly the slight but uniform non-linearity of water substances versus the observable linearity of oil substances. More particularly, curve 130 represents seawater of 35 PPT salinity, while the curve 132 immediately therebeneath represents distilled water. The remaining four curves all represent oil products and are as follows: line 134 represents Skelly "S" crude oil; line 136 is for a crude classified as Lakehead crude oil; line 138 represents a Skelly oil "T" crude oil; and, line 140 represents Mobil regular gasoline. Thus, a mixture consisting of any water and any selected oil product will exhibit a very nearly linear gradation as to speed of sound therethrough along a selected temperature gradient. Any non-linearization contributed by the water constituent is then subject to regression correction through any of several well-known estimation techniques. The result has proven to be sufficiently reliable to enable determination of oil-water cut in percentage over the full range of zero to one hundred percent with sufficient accuracy to enable simultaneous calculation or analog readout of flow rate and, subsequently, volume of oil versus volume of water per unit time.

Changes may be made in the combination and arrangement of elements as heretofore set forth in the specification and shown in the drawings; it being understood that changes may be made in the embodiments disclosed without departing from the spirit and scope of the invention.

What is claimed is:

1. A method of determining quantitative and volumetric data of an oil-water mixture flowing through a conduit of predetermined cross-sectional size, comprising the steps of:

providing in said conduit a metering section of the same cross-sectional size and deriving therein by use of a sonic flow meter with the speed of sound of sonic energy transmitted through the flowing oil-water mixture by determining both an upstream frequency and a downstream frequency of ultrasonic energy transmitted through the flowing oil-water mixture, deriving from said upstream and downstream frequencies and average frequency which varies in direct proportion to the percent water cut from 0 to 100 percent, and deriving from said upstream and downstream frequencies the difference frequency which varies in direct proportion to the rate of flow of flowing oil-water mixture; and placing upstream of the metering section mixing and turbulence-reducing elements within the flowing oil-water mixture; and comparing the derived sonic frequency relative to a proportional empirically derived range of sonic frequencies to determine the percentage of water and oil which is present in the flowing oil-water mixture; and further characterized to include the steps of:
sensing proximate the metering conduit section, the temperature of the oil-water mixture for indication of temperature correction factor; and applying all derived parameters of the flowing oil-water mixture, which includes temperature, velocity of sound energy through the flowing oil-water mixture, and the upstream and downstream frequency difference, for data input to a digital computer and subsequent processing to derive water content of the flowing oil-water mixture over the range from 0 to 100 percent water, as well as flow rate for individual oil and water rates and time-integrated data indicating oil and water volumes.

2. Apparatus for determining the oil and water content in an oil-water mixture flowing through a closed conduit system, comprising:
a metering conduit section of known cross-sectional size inserted in said conduit system;
a fluid mixer conduit section inserted in said conduit system upstream from said metering conduit section;
means attached to said metering conduit section for determining upstream and downstream frequency of sonic energy transmitted at predetermined frequency through said flowing oil-water mixture;
means for converting the upstream and downstream frequency signals to an analog voltage indicative of average frequency which analog voltage varies in proportion to the speed of sound in the mixture; and
means for indicating said analog voltage relative to the calibrated limits of the speed of sound within an oil-water mixture which may vary from zero to one hundred percent water cut.

3. Apparatus as set forth in claim 2 wherein said fluid mixer conduit section comprises:
a mixer element disposed in said conduit section to receive and tortuously route said flowing oil-water mixture; and
a plurality of parallel straightening vanes disposed in said conduit section immediately downsteam from said mixer element.

4. Apparatus as set forth in claim 2 wherein said means for determining upstream and downstream frequency of sonic energy comprises:
a sonic energy flowmeter of the type which provides reciprocal upstream and downstream transmission and reception of sonic energy at predetermined transmission frequency to provide indication of velocity of sound within the oil-water mixture, and to provide rate of flow of the oil-water mixture.

5. Apparatus as set forth in claim 2 wherein said means for determining upstream and downstream frequency of sonic energy comprises:
means for transmitting predetermined frequency of sonic energy for reception downstream to derive a downstream frequency, and means for transmitting said same frequency of sonic energy for reception upstream to derive an upstream frequency;
means for converting each of said upstream and downstream frequencies to respective first and second analog voltages;
means for averaging said first and second analog voltages to produce a speed of sound signal; and
means for recording said analog speed of sound signal relative to calibrated limits of sound speed variation from zero to one hundred percent water cut.

6. Apparatus as set forth in claim 5 which is further characterized to include:
means disposed in said metering conduit section for sensing temperature of said flowing oil-water mixture, said means providing electrical output thereof;
pyrometer amplifier means receiving said temperature electrical output to generate an indicative analog signal output; and
means for indicating and recording said temperature indication.

7. Apparatus as set forth in claim 5 which is further characterized to include:
difference amplifier means receiving input of said first and second analog voltage outputs to produce a difference analog voltage output; and
means for calibrating and recording said difference analog voltage to indicate the relative flow rate of said oil-water mixture.

8. Apparatus as set forth in claim 7 which is further characterized to include:
means disposed in said metering conduit section for sensing temperature of said flowing oil-water mixture, said means providing electrical output thereof;
pyrometer amplifier means receiving said temperature electrical output to generate an indicative analog signal output; and
means for indicating and recording said temperature indication.

9. Apparatus As set forth in claim 8 which further comprises:
means converting said difference frequency voltage output to a difference digital signal;
means converting said average frequency voltage output to an average digital signal;
means providing a digital temperature signal from said pyrometer amplifier means; and
digital computation means receiving input of said difference, average and temperature digital signals to provide output indication of percent oil, percent water, flow rate, volume of oil and volume of water of the flowing oil-water mixture.

* * * * *

UNITED STATES PATENT OFFICE
CERTIFICATE OF CORRECTION

PATENT NO. : 4,080,837
DATED : March 28, 1978
INVENTOR(S) : John A. Alexander and Philip W. Reed It is certified that error appears in the above-identified patent and that said Letters Patent are hereby corrected as shown below:

Column 2, line 67, insert --transducer B(24-- between "transmitting" and ")"

Column 3, line 19, "Fhd A" should be --$F_A$--

Column 3, line 55, "v" should be --V--

Column 4, line 21, "verts" should be --verters--

Signed and Sealed this

Eighth Day of August 1978

[SEAL]

Attest:

RUTH C. MASON
Attesting Officer

DONALD W. BANNER
Commissioner of Patents and Trademarks